United States Patent
Devens, Jr. et al.

(10) Patent No.: US 8,298,220 B2
(45) Date of Patent: Oct. 30, 2012

(54) CRYOPROBE WITH COAXIAL CHAMBERS

(75) Inventors: Douglas A. Devens, Jr., Highland Park, IL (US); David W. Vancelette, San Diego, CA (US); Michael W. V. Perkins, Minnetonka, MN (US)

(73) Assignee: CooperSurgical, Inc., Trumball, CT (US)

( * ) Notice: Subject to any disclaimer, the term of this patent is extended or adjusted under 35 U.S.C. 154(b) by 1384 days.

(21) Appl. No.: 11/940,665

(22) Filed: Nov. 15, 2007

(65) Prior Publication Data

US 2008/0119837 A1  May 22, 2008

Related U.S. Application Data

(60) Provisional application No. 60/866,320, filed on Nov. 17, 2006.

(51) Int. Cl.
*A61B 18/18* (2006.01)
(52) U.S. Cl. ........................................................ 606/23
(58) Field of Classification Search .............. 606/20–26
See application file for complete search history.

(56) References Cited

U.S. PATENT DOCUMENTS

| | | | |
|---|---|---|---|
| 5,207,674 A * | 5/1993 | Hamilton ........................ | 606/20 |
| 5,275,595 A | 1/1994 | Dobak, III | |
| 5,716,353 A | 2/1998 | Matsuura et al. | |
| 5,758,505 A | 6/1998 | Dobak, III et al. | |
| 5,910,104 A | 6/1999 | Dobak, III et al. | |
| 6,035,657 A | 3/2000 | Dobak, III et al. | |
| 6,151,901 A | 11/2000 | Dobak, III et al. | |
| 6,182,666 B1 | 2/2001 | Dobak, III | |
| 6,193,644 B1 | 2/2001 | Dobak, III et al. | |
| 6,237,355 B1 | 5/2001 | Li | |
| 6,241,722 B1 | 6/2001 | Dobak et al. | |
| 6,270,494 B1 | 8/2001 | Kovalcheck et al. | |
| 6,306,129 B1 | 10/2001 | Little et al. | |
| 6,451,012 B2 | 9/2002 | Dobak, III | |
| 6,471,694 B1 | 10/2002 | Kudaravalli et al. | |
| 6,475,212 B2 | 11/2002 | Dobak, III et al. | |
| 6,530,234 B1 | 3/2003 | Dobak, III et al. | |
| 6,878,204 B1 | 4/2005 | Kinnison et al. | |
| 7,381,208 B2 | 6/2008 | van der Walt et al. | |
| 2007/0149957 A1* | 6/2007 | Ross et al. ........................ | 606/21 |
| 2007/0277550 A1 | 12/2007 | Lie et al. | |
| 2008/0027422 A1 | 1/2008 | Vancelette et al. | |
| 2008/0114344 A1 | 5/2008 | Xiao et al. | |
| 2008/0114347 A1* | 5/2008 | Devens et al. ................... | 606/23 |
| 2008/0119833 A1 | 5/2008 | Vancelette et al. | |
| 2008/0119837 A1 | 5/2008 | Devens et al. | |
| 2008/0119838 A1 | 5/2008 | Vancelette et al. | |
| 2008/0119840 A1 | 5/2008 | Vancelette et al. | |

* cited by examiner

*Primary Examiner* — Melanie Hand
(74) *Attorney, Agent, or Firm* — Fish & Richardson P.C.

(57) ABSTRACT

The present disclosure is directed to a cryoprobe capable of improving the cooling power of a cryosurgical system. A representative cryoprobe can comprise an inner cooling chamber and a radial chamber, positioned between the inner cooling chamber and an exterior wall of the cryoprobe. Preferably, the radial chamber is formed to have a low thermal conductivity so as to significantly reduce the transfer of heat between the body and the refrigerant in the inner chamber during a cryosurgical procedure. The radial chamber can be fabricated such that a vacuum can be applied to the radial chamber to further reduce heat transfer between the body and the inner cooling chamber. The radial chamber extends partially along the length of the cryoprobe such that inner cooling chamber is in direct thermal contact with the exterior wall at a cryoprobe tip.

18 Claims, 3 Drawing Sheets

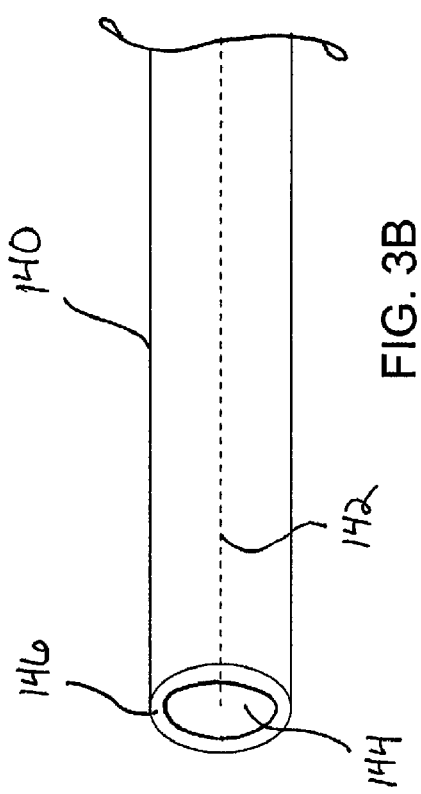
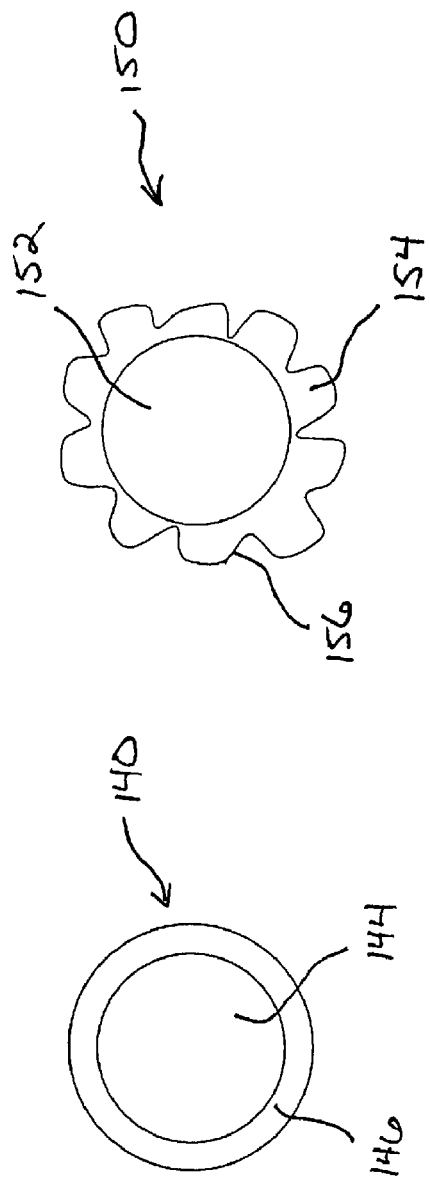
FIG. 3B
FIG. 3A
FIG. 4

CRYOPROBE WITH COAXIAL CHAMBERS

PRIORITY CLAIM

The present application claims priority to U.S. Provisional Application Ser. No. 60/866,320, filed Nov. 17, 2006 and entitled "CRYOPROBE WITH COAXIAL CHAMBERS", which is herein incorporated by reference in its entirety.

FIELD OF THE INVENTION

The present disclosure relates to cryoprobes for use in cryosurgical systems for treatment of benign or cancerous tissues. In particulate, the present disclosure related to a cryoprobe capable of improving the cooling performance of a cryosurgical treatment system by reducing the heating effect of body temperature on a return coolant line.

BACKGROUND OF THE INVENTION

Cryosurgical probes are used to treat a variety of diseases. Cryosurgical probes quickly freeze diseased body tissue, causing the tissue to die after which it will be absorbed by the body, expelled by the body, sloughed off or replaced by scar tissue. Cryothermal treatment can be used to treat prostate cancer and benign prostate disease. Cryosurgery also has gynecological applications. In addition, cryosurgery may be used for the treatment of a number of other diseases and conditions including, but certainly not limited to, breast cancer, liver cancer, renal cancer, glaucoma and other eye diseases.

A variety of cryosurgical instruments variously referred to as cryoprobes, cryosurgical probes, cryosurgical ablation devices, cryostats and cryocoolers have been used for cryosurgery. These devices typically use the principle of Joule-Thomson expansion to generate cooling. They take advantage of the fact that most fluids, when rapidly expanded, become extremely cold. In these devices, a high pressure gas mixture is expanded through a nozzle inside a small cylindrical shaft or sheath typically made of steel. The Joule-Thomson expansion cools the steel sheath to a cold temperature very rapidly. The cryosurgical probes then form ice balls which freeze diseased tissue. A properly performed cryosurgical procedure allows cryoablation of the diseased tissue without undue destruction of surrounding healthy tissue.

SUMMARY OF THE INVENTION

The present disclosure is directed to a cryoprobe capable of improving the cooling power of a cryosurgical system. A representative cryoprobe can comprise an inner cooling chamber and a radial chamber, positioned between the inner cooling chamber and an exterior wall of the cryoprobe. Preferably, the radial chamber is formed to have a low thermal conductivity so as to significantly reduce the transfer of heat between the body and the refrigerant in the inner chamber during a cryosurgical procedure. In one presently preferred embodiment, the radial chamber can be fabricated such that a vacuum can be applied to the radial chamber to further reduce heat transfer between the body and the inner cooling chamber. In one presently contemplated embodiment, the radial chamber extends partially through the length of the cryoprobe such that inner cooling chamber is in direct thermal contact with the exterior wall at a cryoprobe tip.

According to one aspect of the present disclosure, a cryoprobe for use in a cryosurgical system can comprise at least two coaxial chambers. An inner cooling chamber directs refrigerant into and out of a cryoprobe tip portion for forming an iceball at the cryoprobe tip during a freeze cycle. A radial chamber having a low thermal conductivity at least partially surrounds the inner chamber along the length of the cryoprobe so as to significantly reduce heat transfer between the refrigerant in the inner cooling chamber and the body. In some embodiments, the thermal conductivity of the radial chamber can be reduced through introduction of a vacuum within the radial chamber or alternatively, by insulating the radial chamber with an insulating material such as, for example, an aerogel or foam. By reducing the heat transfer across the radial chamber, the refrigerant leaving the cryoprobe tip portion remains cooler, thereby reducing the amount of heat transferred to the high pressure refrigerant entering the cryoprobe tip portion. As the high pressure refrigerant remains cooler at the tip portion, a greater cooling ability is present at the tip portion during the freeze cycle.

In another aspect of the present disclosure, a method for improving the cooling performance of a cryosurgical treatment system can comprise the formation of a coaxial chamber within a cryoprobe. An inner cooling chamber can be formed so as to provide a delivery and return path to a tip portion for a high pressure refrigerant. A radial chamber having a reduced thermal conductivity can surround the inner cooling chamber along at least a portion of the cryoprobe so as to reduce heat transfer between the body and the high pressure refrigerant. In some embodiments, the method can further comprise drawing a vacuum within the radial chamber or alternatively, insulating the radial chamber. By reducing the heat transfer between the body and the inner cooling chamber, the cooling ability at the cryoprobe tip is enhanced.

In yet another aspect of the present disclosure, a cryosurgical treatment system having an improved cooling ability at a cryoprobe tip can include a cryoprobe having dual coaxial chambers within the cryoprobe. The cryosurgical treatment system can deliver a high pressure refrigerant to the cryoprobe tip through an inner cooling chamber, while a radial chamber extending at least partially along the length of the cryoprobe reduces heat transfer between the body and the inner cooling chamber. The thermal conductivity of the radial chamber can be reduced by drawing a vacuum within the radial chamber or by insulating the radial chamber with a suitable insulating material. By reducing the heat transfer between the body and the inner cooling chamber, the high pressure refrigerant is cooler when it reaches the cryoprobe tip, thus increasing the cooling power of the cryoprobe.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE FIGURES

These as well as other objects and advantages of this invention, will be more completely understood and appreciated by referring to the following more detailed description of the presently preferred exemplary embodiments of the invention in conjunction with the accompanying drawings of which:

FIG. 3A is a cross-sectional view of an embodiment of a cryoprobe having coaxial dual chambers according to the present disclosure.

FIG. 3B is perspective, side view of a portion of the cryoprobe of FIG. 3A.

FIG. 4 is a cross-sectional view of an embodiment of a cryoprobe having coaxial dual chambers according to the present disclosure.

DETAILED DESCRIPTION

Figure 1:
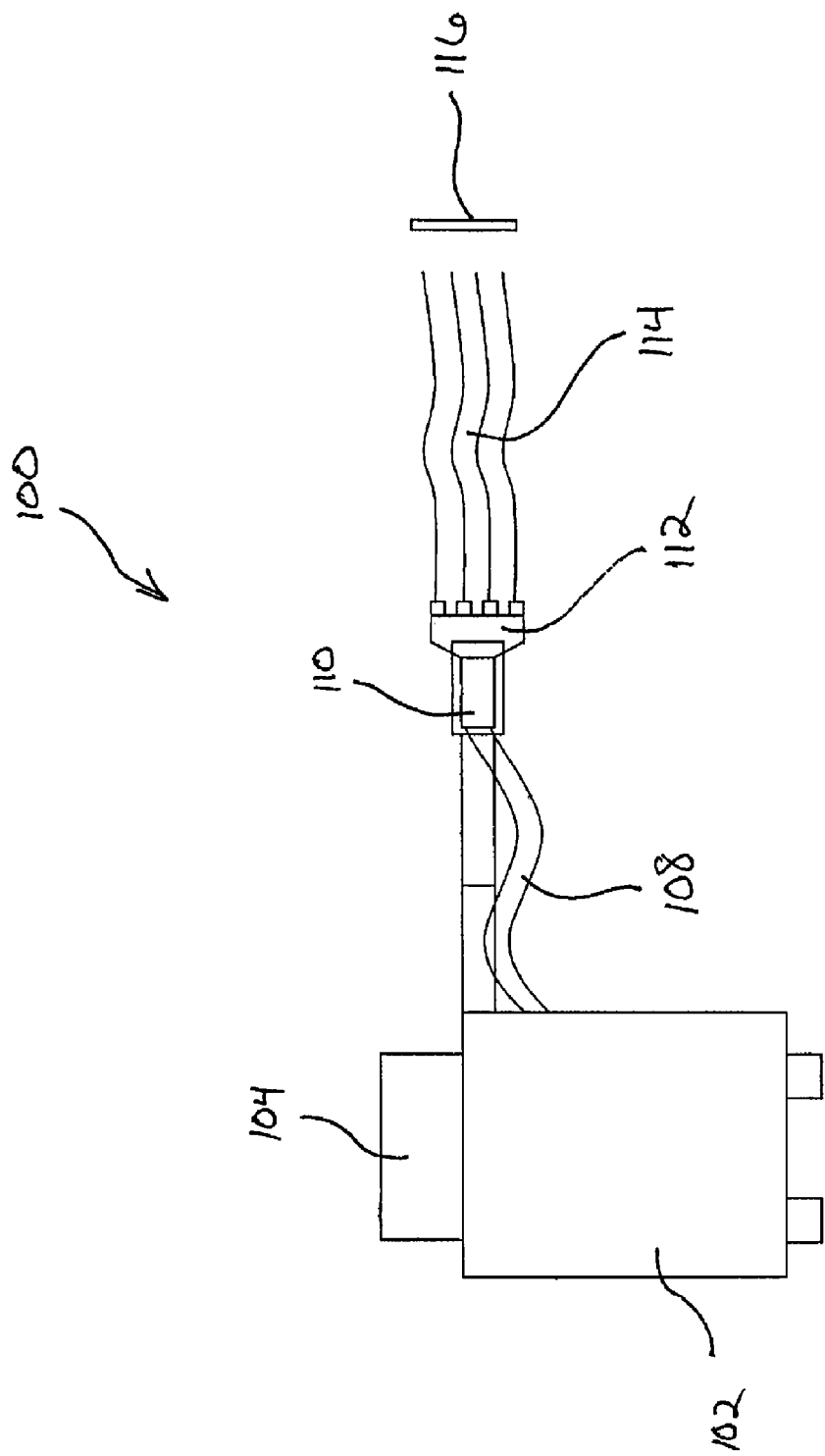
FIG. 1 is a side view of an embodiment of a representative cryosurgical system in which cryoprobes of the present disclosure may be used.

A representative embodiment of a closed loop cryosurgical system 100 that can be used with cryoprobes according to the present disclosure is illustrated generally in FIG. 1. Cryosurgical system 100 can include a refrigeration and control console 102 with an attached display 104. Control console 102 can contain a primary compressor to provide a primary pressurized, mixed gas refrigerant to the system and a secondary compressor to provide a secondary pressurized, mixed gas refrigerant to the system. The use of mixed gas refrigerants is generally known in the art to provide a dramatic increase in cooling performance over the use of a single gas refrigerant. Control console 102 can also include controls that allow for the activation, deactivation, and modification of various system parameters, such as, for example, gas flow rates, pressures, and temperatures of the mixed gas refrigerants. Display 104 can provide the operator the ability to monitor, and in some embodiments adjust, the system to ensure it is performing properly and can provide real-time display as well as recording and historical displays of system parameters. One exemplary console that can be used with an embodiment of the present invention is used as part of the Her Option® Office Cryoablation Therapy available from American Medical Systems of Minnetonka, Minn.

With reference to FIG. 1, the refrigerant is transferred from control console 102 to a cryostat heat exchanger module 110 through a flexible line 108. The cryostat heat exchanger module 110 can include a manifold portion 112 that transfers refrigerant into and receives refrigerant out of one or more cryoprobes 114. The cryostat heat exchanger module 110 and cryoprobes 114 can also be connected to the control console 102 by way of an articulating arm 106, which can be manually or automatically used to position the cryostat heat exchanger module 110 and cryoprobes 114. Although depicted as having the flexible line 108 as a separate component from the articulating arm 106, cryosurgical system 100 can incorporate the flexible line 108 within the articulating arm 106. A positioning grid 116 can be used to properly align and position the cryoprobes 114 for patient insertion.

Figure 2:
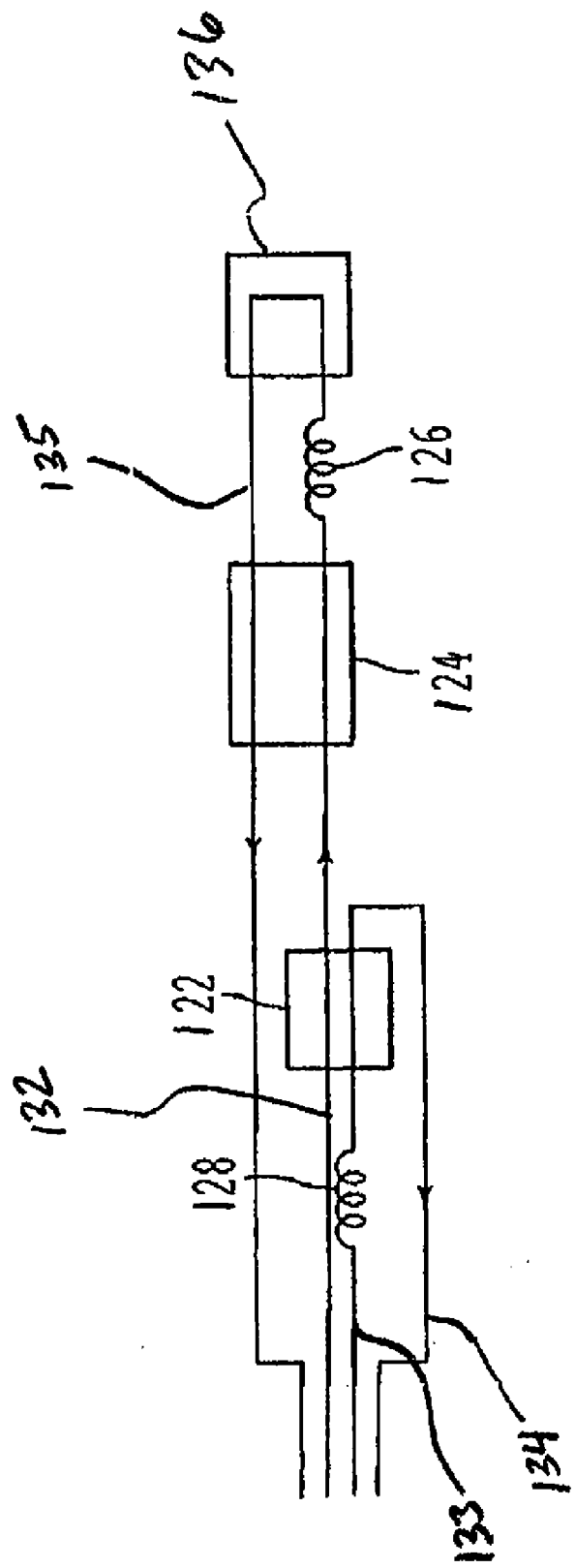
FIG. 2 is a schematic illustration of an embodiment of a cooling system for use with the cryosurgical system of FIG. 1.

As illustrated in FIG. 2, cryosurgical system 100 can comprise both a pre-cool heat exchanger or pre-cooler 122, and a recuperative heat exchanger or recuperator 124. Pre-cooler 122 and recuperator 124 are typically located within the cryostat heat exchanger module 110, but one or both can alternatively be located in the control console 102 or within the cryoprobes 114 themselves.

High pressure primary refrigerant enters the pre-cooler 122 along pathway 132 and is cooled by high pressure secondary refrigerant that enters the pre-cooler 122 along pathway 133 and is then expanded using a Joule-Thomson expansion element 128 to further lower the temperature of the high pressure primary refrigerant. The Joule-Thomson expansion element can comprise a variety of forms such as, for example, a capillary tube, and is fluidly positioned along pathway 133. The expanded low pressure secondary refrigerant then returns to the secondary compressor within the control console 102 along pathway 134 to be repressurized. The high pressure primary refrigerant continues into the recuperator 124 where it is further cooled by low pressure primary refrigerant returning from the tip portion 136 of a cryoprobe 114 along pathway 135. The low pressure primary refrigerant is colder than the high pressure primary refrigerant because it has undergone Joule-Thompson expansion in an expansion element 126 either in or near the cryoprobe tip portion 136. Tip portion 136 constitutes the region of each cryoprobe 114 that performs the actual cryogenic treatment through formation of an iceball at tip portion 136. The low pressure primary refrigerant then continues along pathway 135 where it returns to the control console 102 to be repressurized.

As illustrated in FIGS. 3A and 3B, an embodiment of a cryoprobe 140 of the present disclosure can comprise at least two chambers oriented along a longitudinal axis 142 of the cryoprobe 140. An inner cooling chamber 144 can contain the Joule-Thompson expansion element 126 through which the high pressure primary refrigerant is expanded before it cools the cryoprobe tip portion 136. Following the cooling at cryoprobe tip portion 136, the resulting low pressure primary refrigerant flows back to the console 102 through the inner cooling chamber 144 where the low pressure primary refrigerant is repressurized. A radial chamber 146 surrounds the inner cooling chamber 144 along at least a portion of the longitudinal axis 142. In one representative embodiment, the radial chamber 146 can be fabricated so as to accommodate drawing a vacuum within the radial chamber 146. In another alternative embodiment, the radial chamber 146 can be fabricated to include an insulating material such as, for example, an aerogel or foam. Radial chamber 146 represents a barrier of low thermal conductivity surrounding the inner cooling chamber 144 where the primary refrigerant flows. Preferably, the radial chamber 146 does not extend the full length of the cryoprobe 140 but is instead terminated prior to cryoprobe tip portion 136 so as to not interfere with the formation of an iceball at the cryoprobe tip portion 136.

Through the use of a radial chamber 146 formed to have a low thermal conductivity, the temperature of the returning, low pressure primary refrigerant can be reduced so as to provide additional cooling to the high pressure primary refrigerant prior to reaching the cryoprobe tip portion 136. The low pressure primary refrigerant absorbs significantly less heat from the body due to the low thermal conductivity of the radial chamber 146 as opposed to the heat transfer through the relatively conductive metal inner chamber 144. As such, the returning, low pressure primary refrigerant is colder when it bypasses the high pressure primary refrigerant in the tip portion 136 or recuperator 124. This allows the low pressure primary refrigerant to convect more heat from the high pressure primary refrigerant, which, in turn, creates more cooling at the cryoprobe tip. Cryoprobe 140 can be used in conjunction with precooler 122 in the cryostat heat exchanger module 110 to increase cooling or cryoprobe 140 can be used to replace the increased cooling provided by precooler 122.

As illustrated in FIG. 4, an alternative embodiment of a cryoprobe 150 can again include at least two chambers, an inner cooling chamber 152 and a radial chamber 154, oriented along longitudinal axis 142. The radial chamber 154 can comprise an irregularly shaped perimeter 156 selected to further reduce the low thermal conductivity of the radial chamber chamber 154. Irregularly shaped perimeter 156 can comprise any suitable profile and in some embodiment, can be produced through profile extrusion such that the radial chamber 154 can be furnace brazed to the inner cooling chamber 152. Heat transfer through the radial chamber 154 can be further reduced by drawing a vacuum within the radial chamber 154 or by insulating the radial chamber 154 with a suitable insulating material.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

The invention claimed is:

1. A cryoprobe for use in a cryosurgical system, comprising:
   a tip portion configured to form an iceball to freeze selected tissue during a cryosurgical procedure;
   an inner cooling chamber oriented along a longitudinal axis of the cryoprobe and extending the length of the cryoprobe, the inner cooling chamber configured to deliver refrigerant into and out of the tip portion for forming the one or more iceballs; and
   a radial chamber positioned between the inner cooling chamber and an exterior wall of the cryoprobe, the radial chamber extending coaxially with and surrounding the inner cooling chamber along at least a portion of the length of the cryoprobe, wherein the radial chamber is terminated prior to the tip portion.

2. The cryoprobe of claim 1, wherein the inner chamber includes a Joule-Thompson expansion element for expanding the refrigerant.

3. The cryoprobe of claim 1, wherein the inner cooling chamber is in direct thermal contact with the exterior wall in the tip portion of the cryoprobe.

4. The cryoprobe of claim 1, wherein the radial chamber is vacuum insulated.

5. The cryoprobe of claim 1, wherein the radial chamber includes an insulating material.

6. The cryoprobe of claim 5, wherein the insulating material is selected from the group consisting of aerogel and foam.

7. The cryoprobe of claim 1, wherein the exterior wall has a constant outer perimeter.

8. The cryoprobe of claim 1 wherein the exterior wall has an irregular outer perimeter.

9. A cryosurgical treatment system comprising:
   a console having a primary compressor for pressurizing a primary refrigerant; and
   one or more cryoprobes fluidly connected to the console, each cryoprobe comprising a tip portion configured to be cooled by the primary refrigerant to freeze selected tissue during a cryosurgical procedure, an inner cooling chamber oriented along a longitudinal axis of each cryoprobe through which the primary refrigerant flows into and out of the tip portion, and a radial chamber positioned between the inner cooling chamber and an exterior wall of the cryoprobe, the radial chamber extending coaxially with and surrounding the inner cooling chamber along at least a portion of the length of the cryoprobe, wherein the radial chamber of each cryoprobe is terminated prior to the tip portion such that the inner cooling chamber is in direct thermal contact with the exterior wall in the tip portion.

10. The system of claim 9, further comprising a recuperative heat exchanger configured to cool the primary refrigerant flowing from the console with primary refrigerant returning from the one or more cryoprobes.

11. The system of claim 10, wherein the console further includes a secondary compressor for pressurizing a secondary refrigerant, and the system further comprises a pre-cool heat exchanger configured to expand the secondary refrigerant and cool the primary refrigerant flowing from the console with the expanded secondary refrigerant before returning the secondary refrigerant to the secondary compressor to be repressurized.

12. The system of claim 9, wherein the inner cooling chamber of each cryoprobe includes a Joule-Thompson expansion element for expanding the primary refrigerant.

13. The system of claim 9, wherein the radial chamber is vacuum insulated.

14. The system of claim 9, wherein the radial chamber includes an insulating material.

15. A method for improving the cooling performance of a cryosurgical treatment system comprising:
   forming a cryoprobe having a radial chamber surrounding an inner cooling chamber, the radial chamber terminating prior to a tip portion fluidly interconnected to the inner cooling chamber;
   delivering a refrigerant fluid to the tip portion through the inner cooling chamber, the refrigerant fluid cooling the tip portion so as to form an iceball at the tip portion.

16. The method of claim 15, further comprising:
drawing a vacuum within the radial chamber.

17. The method of claim 15, further comprising:
insulating the radial chamber.

18. The method of claim 15, further comprising:
expanding the refrigerant fluid within an expansion element in the inner cooling chamber prior to delivering the refrigerant fluid to the tip portion.

* * * * *

UNITED STATES PATENT AND TRADEMARK OFFICE
CERTIFICATE OF CORRECTION

PATENT NO. : 8,298,220 B2
APPLICATION NO. : 11/940665
DATED : October 30, 2012
INVENTOR(S) : Douglas A. Devens, Jr.

Page 1 of 1

It is certified that error appears in the above-identified patent and that said Letters Patent is hereby corrected as shown below:

Title page, Item [73] (Assignee):
delete "Trumball, CT (US)" and replace with --Trumbull, CT (US)--.

Signed and Sealed this
Fifteenth Day of January, 2013

David J. Kappos
*Director of the United States Patent and Trademark Office*